United States Patent
Grönberg

(10) Patent No.: US 9,901,348 B2
(45) Date of Patent: Feb. 27, 2018

(54) MOUNTING TOOL FOR AN ANASTOMOTIC DEVICE

(71) Applicant: CARPONOVUM AB, Halmstad (SE)

(72) Inventor: Anders Grönberg, Halmstad (SE)

(73) Assignee: CARPONOVUM AB, Halmstad (SE)

( * ) Notice: Subject to any disclaimer, the term of this patent is extended or adjusted under 35 U.S.C. 154(b) by 344 days.

(21) Appl. No.: 14/428,747

(22) PCT Filed: Sep. 12, 2013

(86) PCT No.: PCT/SE2013/051065
§ 371 (c)(1),
(2) Date: Mar. 17, 2015

(87) PCT Pub. No.: WO2014/046596
PCT Pub. Date: Mar. 27, 2014

(65) Prior Publication Data
US 2015/0230798 A1    Aug. 20, 2015

(30) Foreign Application Priority Data
Sep. 20, 2012  (SE) ..................................... 1251060

(51) Int. Cl.
*A61B 17/115* (2006.01)
*A61B 17/11* (2006.01)

(52) U.S. Cl.
CPC ......... *A61B 17/115* (2013.01); *A61B 17/1114* (2013.01)

(58) Field of Classification Search
CPC .... A61B 17/08; A61B 17/115; A61B 17/1114
USPC ..................................... 227/176.1, 175.1, 19
See application file for complete search history.

(56) References Cited

U.S. PATENT DOCUMENTS

| 6,503,259 B2* | 1/2003 | Huxel | A61B 17/0643 227/179.1 |
| 7,527,185 B2* | 5/2009 | Harari | A61B 17/0643 227/179.1 |
| 2004/0195289 A1* | 10/2004 | Aranyi | A61B 17/072 227/180.1 |

FOREIGN PATENT DOCUMENTS

| EP | 0517488 A1 | 12/1992 |
| WO | 2004008936 A2 | 1/2004 |
| WO | 2007122223 A1 | 11/2007 |

* cited by examiner

Primary Examiner — Nathaniel Chukwurah
(74) Attorney, Agent, or Firm — Capitol City TechLaw

(57) ABSTRACT

An anvil (300) for use in connection with a first member (10) of an anastomotic device (100) in the side wall of an intestine is provided. The anvil (300) comprises a distal head portion (301) and a connecting rod (302) extending proximally from the head portion (301). The distal head portion (301) has a first member retaining means (304), being displaceable laterally and centrally between a first member locking position and a first member releasing position. A tool (400) for use in connection with an anvil (300), according to above, is also provided, and a kit of parts comprising the two. The tool (400) comprises a receiving member (401) for receiving the connecting rod (302) of the anvil (300), and a seat (405) for a second member (20) of the anastomotic device (100), said seat (405) being arranged circumferentially of said receiving member (401), and said receiving member (401) being displaceable in relation to said seat (405).

11 Claims, 5 Drawing Sheets

MOUNTING TOOL FOR AN ANASTOMOTIC DEVICE

This application claims priority under 35 USC 119(a)-(d) to SE patent application No. 1251060-8, which was filed on Sep. 20, 2012, the entire content of which is incorporated herein by reference.

TECHNICAL FIELD

The present invention relates to a mounting tool for an anastomotic device, and more particularly, the present invention refers to a mounting tool for arranging an anastomotic device in the side wall of an intestine. Furthermore, the invention relates to a method for mounting the device to a tubular structure.

BACKGROUND OF THE INVENTION

Colorectal cancer is the third most frequent type of cancer in the world having an occurrence of about 1 million new cases every year. The incidents of cancer are considerably more frequent in the industrial part of the world.

Current techniques for mechanically performing anastomosis of hollow organs use circular mechanical staplers, which execute the connection of the tissue edges of the dissected hollow organ by metallic or plastic staples. A wide variety of surgical staplers have been developed for gastric, oesophageal and intestinal surgery. In performing surgical anastomotic stapling, generally two pieces of the hollow organ are joined by a ring of staples with a closed loopstapler. End to end anastomoses are generally performed by intraluminal surgical staplers that deliver a pair of staggered rings of staples. During this process, a circular knife blade is used to separate the tissue that is held within the circular ring. The separated tissue is then removed with the stapler to form a circular opening within the lumen along the stapling line.

A major issue regarding anastomosis healing is the blood circulation of the anastomosis during the healing process. Despite substantial development of surgical techniques during the last decades, morbidity and mortality after resections in the gastrointestinal tract, e.g. due to anastomotic leakage, remain as serious problems. Ischemia and inflammation, which are natural parts of the healing process, may cause leakage and secondary infection that may be fatal for the patient in the stapling area. Therefore, it has become common practice to relieve the pressure from the anastomosis by performing a deviating stoma, especially when the anastomosis is carried out in the lower part of colon and in rectum. By relieving pressure and faecal stream from the anastomosis during the healing process, the leakage incident may be reduced and fatal consequences of anastomotic dehiscence can be avoided. The inconvenience for the patient is obvious, since the patient must have a temporary stoma for a time period of about 3 to 6 months, and then has to undergo a second surgery in order to close the stoma. Unfortunately in many cases, the closure of the stoma cannot be reversed and the patient is forced to live with a permanent stoma leading to lower quality of life associated with increased costs.

Additionally, there is an increased risk of anastomotic stenosis, surgical staplers create a smaller and more rigid opening compared to the cross section of the original lumen due to the staples inside the hollow structure connecting the two ends thereof, i.e. a collar may be formed that may lead to stenosis.

Hence, there has been a need in the technical field to develop assemblies overcoming these disadvantages. One such assembly is disclosed in WO 2007122223, wherein an assembly comprising interlocking members for use in achieving anastomosis of tubular organs is disclosed. The assembly comprises two rigid parts, onto which two elastic rings are arranged, to secure intestine ends, respectively, in between each rigid part and corresponding elastic part, whereafter the rigid parts are interconnected via a connection member. It is however difficult to use such open end anastomotic rings for connecting the side of an intestine to another side or an open end, which is often called for due to tumours with difficult access.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing: an anvil for use in connection with a first member of an anastomotic device in the side wall of an intestine, said anvil comprising a distal head portion and a connecting rod extending proximally from the head portion; said distal head portion having a first member retaining means, being displaceable laterally and centrally between a first member locking position and a first member releasing position; a tool for use in connection with an anvil according to above for arranging an anastomotic device in the sidewall of an intestine, said tool comprising a receiving member for receiving the connecting rod of the anvil, and a seat for a second member of the anastomotic device, said seat being arranged circumferentially of said receiving member, and said receiving member being displaceable in relation to said seat; and a kit of parts comprising said anvil and said tool.

Further objects, features and advantages of the present invention will appear from the following detailed description, from the attached drawings as well as from the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Figure 1:
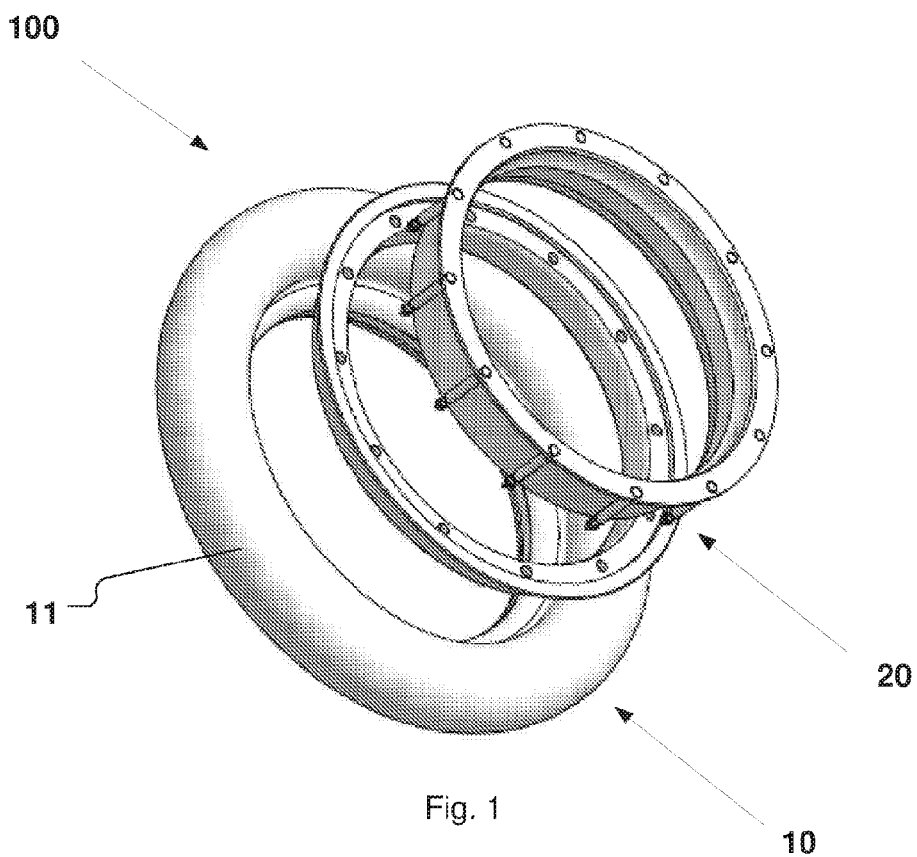
FIG. 1 is a perspective and exploded view of an anastomotic device according to one embodiment of the present invention.
Figure 2:
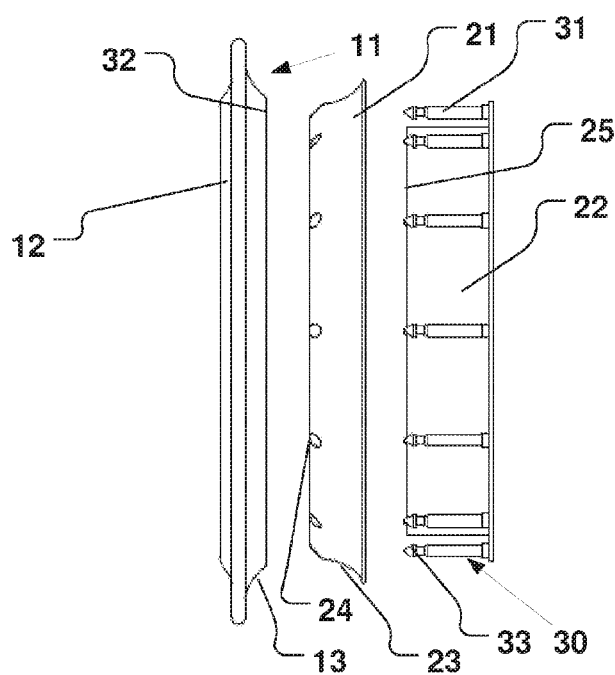
FIG. 2 is a side and exploded view of an anastomotic device according to one embodiment of the present invention.

In FIGS. 1 and 2, a device 100 for connection to the side wall of an intestine is disclosed. This device 100 may then in turn be connected to another such device 100, connected to the side wall of another part of this intestine, or it may be connected to another anastomotic device according to the prior art. The device 100 for arrangement on the side wall of an intestine comprises a first member 10 and a second member 20. The first member 10 and the second member 20 are both of a generally hollow open configuration.

The first member 10 comprises an elastic part 11 and a rigid support part 12, which is disclosed in FIG. 2 (wherein the elastic part 11 has been omitted for clearer view of the other parts). The elastic part 11 is a substantial circular symmetric ring and is made as a compact body or as a tube, which may be filled with air, gas or fluid, and are made of an elastic polymeric material of for example 40 to 70 Shore. The rigid support part 12 may be of a polymeric material, more specifically a biocompatible material and most specifically a biodegradable material, of a rigidity adequate to stabilize the elastic part 11. The elastic part 11 may for example be an elastic ring of a suitable polymeric or rubber material, such as an elastomer. The elastic part 11 has a first and a second axial end. The rigid support part 12 is arranged at the first axial end of the elastic part 11. The rigid support part 12 is also ring shaped, with one side thereof adapted to receive the elastic part 11. This side of the rigid support part 12 may then have an elastic part seat 13. The elastic part seat 13 may be concavely shaped to receive the convex axial end of the elastic part 11. The elastic part 11 may be attached to the rigid support part 12 through glueing or through overmoulding or co-moulding.

During removal of a tumour from an intestine, the affected part of the intestine is removed by cutting the intestine on a suitable distance on each side of the intestine. Depending on where and how the tumour was located, there may be a need to connect the side of one of the free ends of the intestine with a side of the other free end of the intestine, or there may be a need to connect the side of one free end with the other free end. The device according to FIGS. 1 and 2 allows for creating a connection through the side of one such free end.

Figure 3:
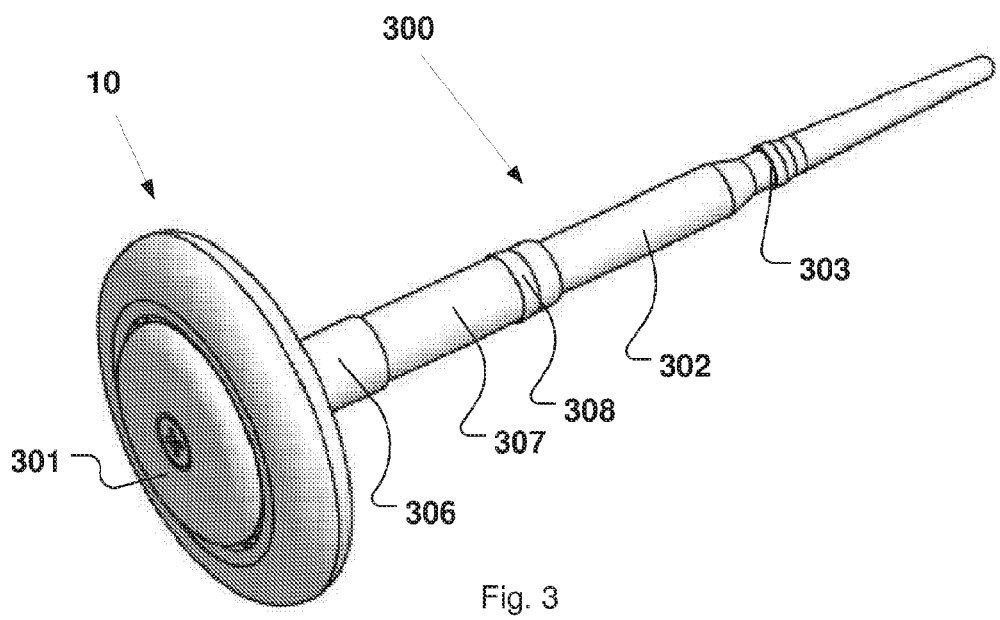
FIG. 3 is a perspective view of an anvil according to one embodiment of the present invention.

When connecting the side of a free end of an intestine, the open end is first closed with sutures. Then the intestine is incised at a suitable position. The device 100 is arranged on an anvil 300, according to FIG. 3.

The anvil 300 comprises a disc shaped head portion 301, which is adapted in size and shape to hold the first member 10 around its periphery. A connecting rod 302, for connection with a tool for arrangement of the second member 20, extends axially from the head portion 301. An incision is made in the side wall of the intestine. Thereafter the disc shaped head portion 301, with a first member 10 arranged thereon, is inserted into the intestine. Subsequently, the side wall of the intestine is sutured, such that only the connecting rod 302 extends laterally away from the intestine.

Figure 4:
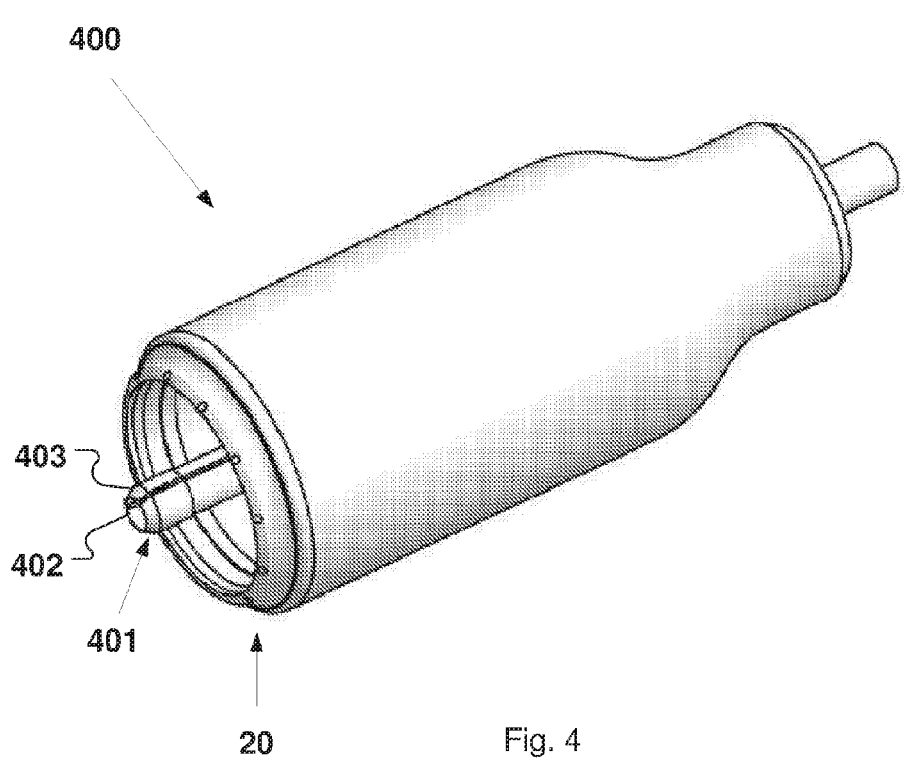
FIG. 4 is a perspective view of a tool according to one embodiment of the present invention.

The connecting rod 302 is then inserted a tool 400 for arrangement of the second member 20, as illustrated in FIG. 4. For this purpose the tool 400 comprises a connecting rod receiving member 401. The connecting rod receiving member 401 comprises a female part 402, with leaves 403 that may snap fit around a locking flange 303 on the anvil 300.

In the lumen of the female part 402 a corresponding locking ridge 404 is positioned, such that the connecting rod 302 may be inserted in the proximal direction into the connecting rod receiving member 401 to force the leaves 403 laterally and outwardly until the locking flange 303 passes proximally of the locking ridge 404, where after the locking ridge 404 snaps back centrally.

Figure 5:
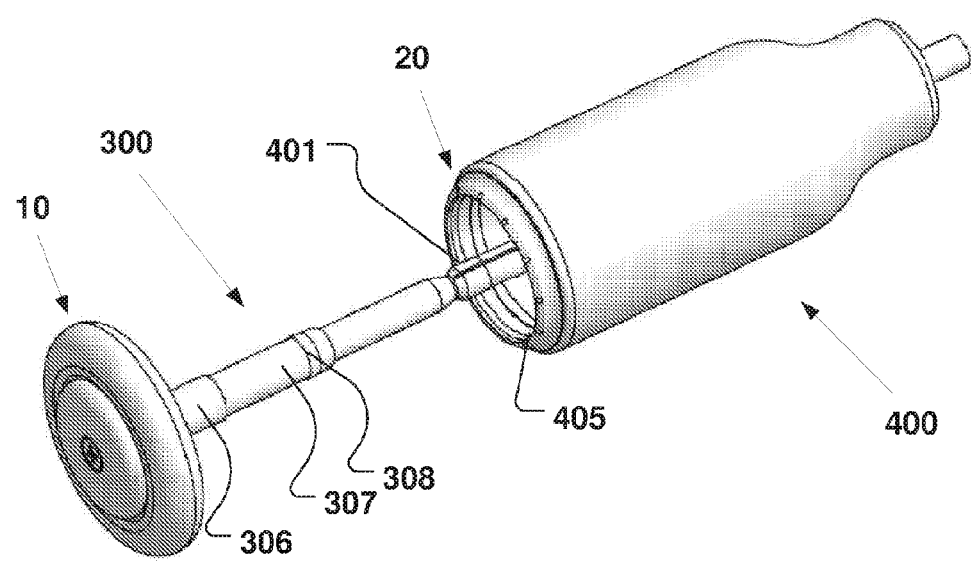
FIG. 5 is a perspective view of an anvil according to one embodiment of the present invention connected to a tool according to one embodiment of the present invention.
Figure 6:
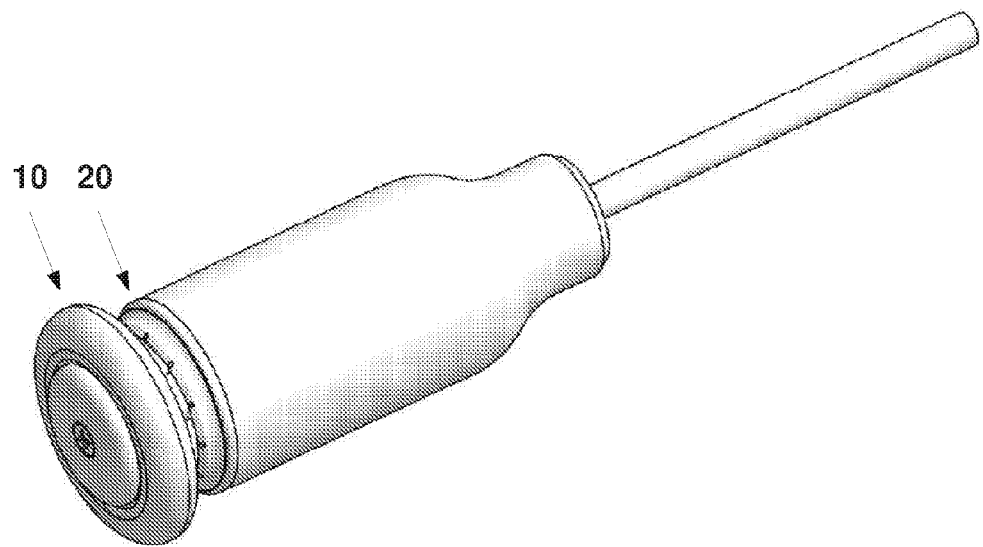
FIG. 6 is a perspective view of an anvil according to one embodiment of the present invention connected to a tool according to one embodiment of the present invention.
Figure 7:
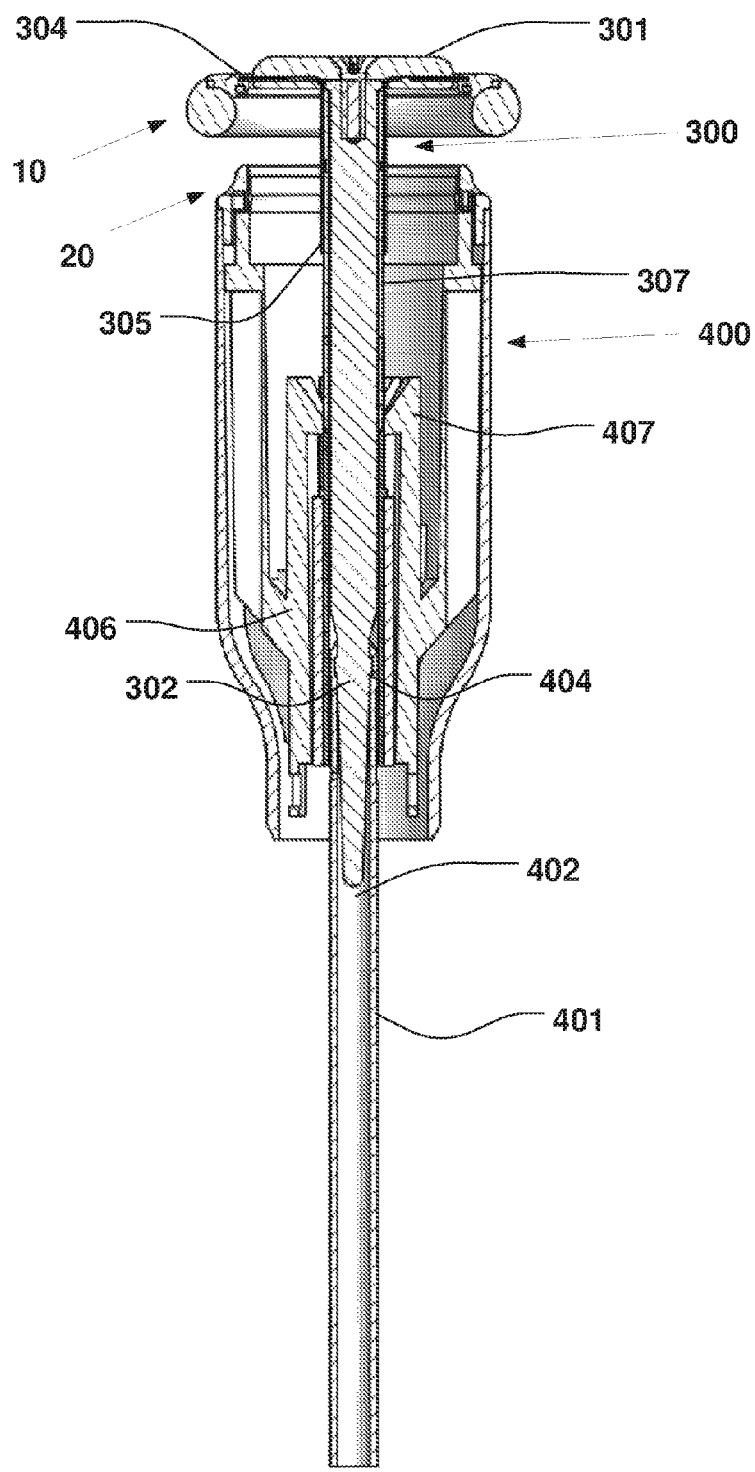
FIG. 7 is a cross sectional view of an anvil according to one embodiment of the invention arranged in a tool according to one embodiment of the present invention.
Figure 8:
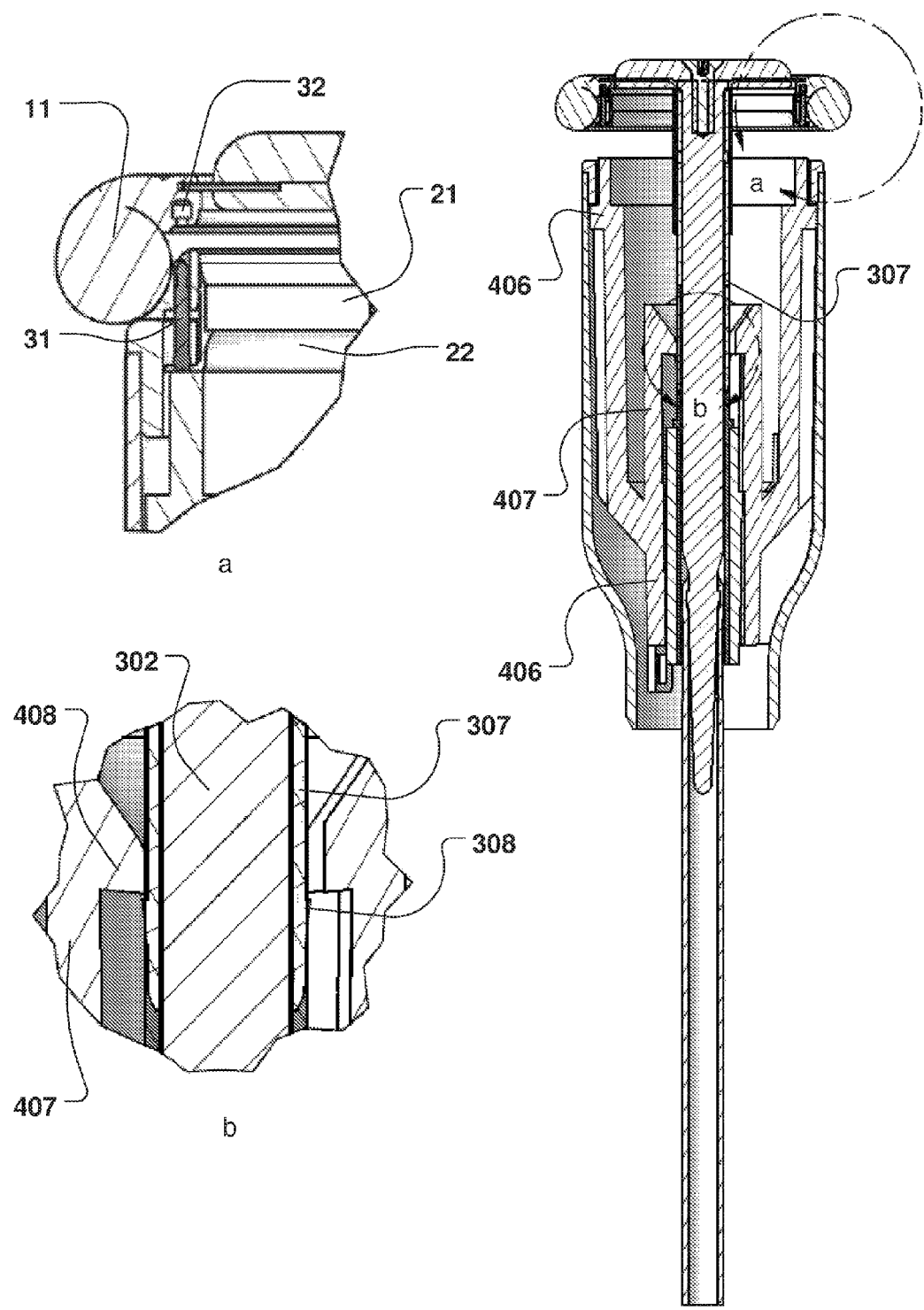
FIG. 8 is a cross sectional view of an anvil according to one embodiment of the invention arranged in a tool according to one embodiment of the present invention, with a close up on the interaction between the two.

In this position, which is illustrated in FIG. 5, the anvil 300 is connected to the tool 400. The connecting rod receiving member 401 may be threaded in its proximal zone, such as to realize proximal movement of the connecting rod receiving member 401 in relation to a second member seat 405, for receiving a second member 20, in the distal end of the tool 400, to thereby drag the anvil 300 into the tool 400 by twisting a twisting knob (not shown) at the distal end zone of the tool 400.

The second member 20 comprises a first and a second axial end. The first end of the second member 20 matches the shape of the second axial end of the elastic part 11, such that an intestine wall may be uniformly distributed between the second axial end of the elastic part 11 and the second member 20. For connecting the first member 10 to the second member 20 a connection member 30 is provided. The connection member 30 may be at least one male part 31 on the second member and at least one female part 32 on the first member 10. In the embodiment disclosed in FIGS. 1 and 2, the male parts 31 on the second member 20 are pins 31, and the rigid support part 12 on the first member 10 comprises corresponding female parts 32 in form of holes or slits 32, such that the second part 20 may be brought into connection with the first part 10 by inserting the pins 31 into the holes or slits 32. The pins 31 on the second part 20 may comprise barbs 33 and the holes or slits 32 on the rigid support part 12 on the first member 110 may have flanges at their mouths, to interlock the first part 10 to the second part 20 at a suitable distance from each other, at which the pressure on the intestine squeezed between the elastic part 11 of the first member 10 and the second member 20.

The second member 20, according to the embodiment in FIGS. 1 and 2, comprises an intestine interacting part 21 and a pin carrying and tissue cutting part 22. The intestine interacting part 21 and a pin carrying and tissue cutting part 22 are preferably made of a polymeric material, more specifically a biocompatible material and most specifically a biodegradable material. The pins 31 extending from the pin carrying part 22 are preferably of a biocompatible metallic material, but rigid polymers are also envisioned. The intestine interacting part 21 has a concave intestine/elastic part seat 23 at its first axial end, intended to face the intestine and the first member 10, such that the round shape of the elastic part 11, shaping the intestine in contact therewith, may sit on the second member 20 in a convenient way. The intestine interacting part 21 has holes or slits 24 and said pin carrying part 22 is provided with the pins 31. The pins 31 are received in the holes or slits 24, such that the pins are accessible to interact with the support part 12 of the first member 10. In this way manufacturing of the second member 20 is facilitated, since it may be difficult to arrange pins on the concave surface of the intestine interacting part 21 while simultaneously arranging said pins to correspond in position and direction to the holes or slits 32 on the rigid support part 12 on the first member 10. Simultaneously, the pin carrying and tissue cutting part 22 is provided with a sharp cutting edge 25, which will cut the intestinal tissue in between the first member 10 and the second member 20, as the pins 31 penetrate the holes or slits 32 of the first member 10.

The anvil 300 is dragged into the tool 400 until the first and the second member 10, 20 interconnects. When bringing the first member 10 and the second member 20 together, as disclosed in FIGS. 5 to 8, the pins 31 will penetrate the wall of the intestine around the incision, where after they will enter the holes or slits 32 on the rigid support part 12 on the first member 10. Then the barbs 33 and the flanges 34 will interact to interlock the first member 10 to the second member 20. In this way the first member 10 and the second member 20 are connected to each other, radially inwards of the elastic part 11, and the intestine wall is squeezed at a uniform pressure between the elastic part 11 of the first member 10 and the concave intestine/elastic part seat 23. This is all realized by twisting the twisting knob in the proximal end of tool 400, until the anvil 300 is dragged into the tool 400 for cooperation between the first member 10 and the second member 20, in accordance with above.

After the first member 10 and the second member 20 has been brought into engagement, in which position the intestine is squeezed in between the elastic part 11 and the second member 20 around the incision, the cutting edge 25 has cut the intestinal tissue in between the first member 10 and the second member 20 when the anvil 300 has been brought into the tool 400 and subsequently into a position wherein the pins 31 penetrate the intestine wall and locks to the first member 10, in accordance with above. The cutting edge 25 is circular and may constitute the inner periphery of the second member 20, but may simultaneously be larger than the circumference of the head portion 301, such that the anvil 300 may be retracted from the intestine. When activated the cutting edge 25 is moved distally in relation to the first member 10 and the intestine interacting part 21, to cut the intestine wall along the inner periphery of the first member 10 and the second member 20. The cutting edge 25 may be moved distally by being arranged on the seat 405 by a pusher 406 on a threaded shaft and then twisting yet another twisting knob (not shown) in the proximal ends of the tool 400 to make the cutting edge 25 via the pusher 406 move distally along the threads. It is also possible to have the pusher 406 suspended on a spring mechanism, such that when said spring is released, the pusher 406 will be thrown distally to cut the intestine.

The anvil 300 is provided with a first member retaining means 304, extending laterally from the circumference of the head portion 301. The retaining means 304 interacts with a corresponding groove on the first member 10, or locks the first member 10 from distal movement by positioning itself distally of the first member 10. The retaining means is displaceable centrally, so as to release the first member 10 from the head portion 301 and thus the anvil 300. In one embodiment the retaining means 304 comprises laterally extending blades, that extend centrally to the connecting rod 302, and then proximally along the connecting rod. When the blades are pulled proximally, they will move centrally from the periphery of the head portion 301 to release the first member 10. To facilitate grasping of the blades/retaining means 304, the blades/retaining means are provided with protrusions 305, such as knobs, such as weldings, at the proximal end thereof along the connecting rod 302. A ring 306 may be arranged laterally of the protrusions 305, to facilitated proximal displacement of the protrusions and thus central withdrawal from the periphery of the head portion 301. The retaining means 304 is in turn connected to a sleeve 307, for example by clamping the retaining means 304 between the ring 306 and the sleeve 307. The sleeve 307 is arranged displaceably on the connecting rod 302. At the proximal end zone of the sleeve 307 a locking flange 308 is positioned.

When the pusher 406 is moved distally to cut the intestine wall via the cutting edge 25, a retaining means 304 interacting member, such as a retaining means connector 407, will be brought into cooperation with the retaining means 304, such that subsequent proximal movement of the cutting element and/or the connector 407, will pull the retaining means 304 proximally along the connecting rod 302 to central withdraw the retaining means 304 from the periphery of the head portion 301 for releasing the first member 10. The retaining means connector 407 may for example comprise a distal locking lip 408 that may be forced outwardly and laterally when being pushed by the locking flange 308, while the anvil 300 is moved proximally into the tool 400. When the flange 308 has passed proximally beyond the locking lip 408 the locking lip 408 snaps centrally on the distal side of the flange 308. Thus, subsequent proximal movement of the connector 407 will result in proximal movement of the retaining means 304, which in turn will move the retaining means 304 centrally from the periphery of the disc shaped head portion 301 of the anvil 300. The retaining means connector 407 may be displaceable proximodistally with regard to said second member seat 405, to move the retaining means 304 from a first member locking position to a first member releasing position. Hence, after the cutting with the cutting edge 25, the pusher 406 is displaced proximally in relation to the first member 10 and the second member 20. Simultaneously, the connector 407 will pull the retaining means 304 proximally to release the first member, and thus also the second member 20 now connected to the first member 10, from the anvil 300. The pusher 406 and the connector 407 may be arranged on a threaded shaft in accordance with above, such that they may be displaced proximally by a twisting action.

When the anvil 300 is subsequently retracted from the intestine, the device 100 has been securely arranged in the side wall of an intestine, and the intestine tissue removed from the lumen of the device 100. In this position, the device 100 may be connected to another device 100 through the use of a separate connector or to an anastomotic device according to the prior art WO2007122223. The separate connector may have a generally hollow open configuration. The separate connector may provided slits extending axially from the free ends thereof around the periphery forming tongues between the slits. Centrally of the slits and tongues a central tubular part is arranged. At least one of the tongues on each side is provided with an outward protrusion arranged adjacent or at a distance from the free ends of the tongues. The central tubular part may be provided with through holes that may be connected to catheters. The catheters have a length allowing for following the intestine out through the anus of the patient, such that air or water may be pushed through the catheters to check the sealing pressure between the elastic parts 11, with accommodated intestine walls there between.

Herein above, several embodiments of the invention are described with reference to the drawings in order to enable a skilled person to perform the invention. However, the features and method steps included in these embodiments do not limit the invention. Moreover, the features and method steps may be combined in other manners than specifically described.

In the claims, the term "comprises/comprising" does not exclude the presence of other elements or steps. Furthermore, although individually listed, a plurality of means, elements or method steps may be implemented. Additionally, although individual features may be included in different embodiments, these may possibly be combined in other ways, and the inclusion in different embodiments does not imply that a combination of features is not feasible. In addition, singular references do not exclude a plurality. The terms "a", "an" does not preclude a plurality. Reference signs in the claims are provided merely as a clarifying example and shall not be construed as limiting the scope of the claims in any way.

The invention claimed is:

1. An anvil for use with a first ring shaped member of an anastomotic device in the side wall of an intestine, the anvil comprising:
   a distal head portion and a connecting rod extending proximally from the distal head portion;
   the distal head portion having first member retaining means for displacement laterally and centrally between a first member locking position and a first member releasing position;
   wherein the first member retaining means comprises laterally extending blades, that extend centrally to the connecting rod, and then proximally along the connecting rod.

2. The anvil according to claim 1, wherein the connecting rod is provided with a locking flange, extending laterally from the connecting rod.

3. The anvil according to claim 1, wherein the blades are provided with protrusions at the proximal end thereof along the connecting rod.

4. The anvil according to claim 3, wherein a ring is arranged laterally of the protrusions.

5. A tool for use in connection with an anvil according to claim 1 for arranging an anastomotic device in the sidewall of an intestine, the tool comprising:
   a receiving member for receiving the connecting rod of the anvil; and
   a seat for a second ring shaped member of the anastomotic device, the seat being arranged circumferentially of the receiving member, and the receiving member being displaceable in relation to the seat.

6. The tool according to claim 5, wherein the receiving member comprises a female part with leaves, and the connecting rod comprises a locking flange proximally of the distal head portion, the leaves being snap fitable around the locking flange.

7. The tool according to claim 6, wherein the female part comprises a locking ridge, corresponding to the locking flange, such that the connecting rod may be inserted in the proximal direction into the receiving member to force the leaves laterally and outwardly until the locking flange passes proximally of the locking ridge, where after the locking ridge snaps back centrally.

8. The tool according to claim 5, wherein the receiving member is threaded in its proximal zone, such as to realize proximal movement of the receiving member in relation to the seat.

9. The tool according to claim 5, further comprising an interacting member that is displaceable proximodistally with regard to the seat, to move the first member retaining means from the first member locking position to the first member releasing position.

10. A kit of parts comprising:
    an anvil according to claim 1; and
    a tool according to claim 5.

11. An anvil for use with an anastomotic device in the side wall of an intestine, the anvil comprising:
    a distal head portion;
    a connecting rod extending from the distal head portion; and
    a retainer mounted on the connecting rod for movement between
       a first position in which the retainer extends radially outward from the distal head portion, and
       a second position in which, relative to the first position, the retainer is located radially inward and further away from the distal head portion;
    wherein the retainer includes laterally extending blades, that extend centrally to the connecting rod, and then proximally along the connecting rod.

* * * * *